United States Patent [19]
Mawhirt et al.

[11] Patent Number: 5,571,132
[45] Date of Patent: Nov. 5, 1996

[54] SELF ACTIVATED FINGER LANCET

[75] Inventors: James A. Mawhirt, Brooklyn, N.Y.;
Anthony F. Kuklo, Jr., Bridgewater, N.J.

[73] Assignee: International Technidyne Corporation, Edison, N.J.

[21] Appl. No.: 465,686

[22] Filed: Jun. 6, 1995

[51] Int. Cl.$^6$ ........................................ A61B 17/32
[52] U.S. Cl. ........................... 606/182; 606/167; 606/181
[58] Field of Search ........................ 606/167, 181, 606/182; 604/192, 194, 198

[56] References Cited

U.S. PATENT DOCUMENTS

| 6,240 | 5/1849 | Ives ........................................ 606/182 |
| 4,203,446 | 5/1980 | Höfert et al. . |
| 4,375,815 | 3/1983 | Burns . |
| 4,388,925 | 6/1983 | Burns . |
| 4,442,836 | 4/1984 | Meinecke et al. . |
| 4,624,253 | 11/1986 | Burns . |
| 4,643,189 | 2/1987 | Mintz . |
| 4,676,244 | 6/1987 | Enstrom . |
| 4,677,979 | 7/1987 | Burns . |
| 4,869,249 | 9/1989 | Crossman et al. . |
| 5,212,879 | 5/1993 | Biro et al. . |
| 5,314,441 | 5/1994 | Cusack et al. . |
| 5,318,584 | 6/1994 | Lange et al. . |
| 5,397,334 | 3/1995 | Schenk et al. ........................ 606/182 |

Primary Examiner—Michael Powell Buiz
Assistant Examiner—Mark S. Leonardo
Attorney, Agent, or Firm—Plevy & Assocaites

[57] ABSTRACT

A self-activated blood drop generator device comprising a casing having an internal hollow and blade assembly disposed within the hollow of the casing for generating an incision in a patient's skin. The device includes a fork-shaped triggering mechanism coupled to the blade assembly for propelling the blade assembly through a predetermined path. A cam arrangement associated with the casing causes the cutting portion of the blade assembly to travel through an arcuate scapel-like path as the cutting portion passes through an aperture in the casing. A retractor arrangement associated with the casing, the blade assembly and the triggering mechanism, are provided for retracting the blade assembly into the hollow of the casing. Also provided is accelerator arrangement associated with the casing and the triggering mechanism for accelerating the triggering mechanism through the hollow of the casing thereby causing the blade assembly to accelerate through the predetermined path. The activation of the device causes the cutting portion of the blade to travel out of the hollow of the casing through the aperture to incise the patient's skin and then retract back through the aperture into the hollow of the casing.

19 Claims, 8 Drawing Sheets

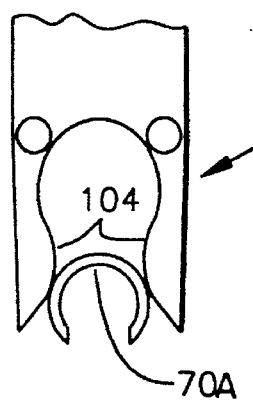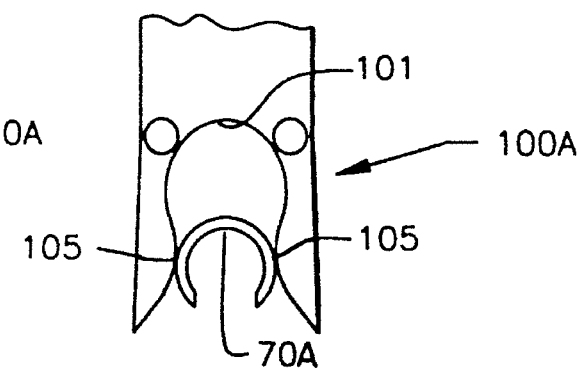
FIG. 6A  FIG. 6B
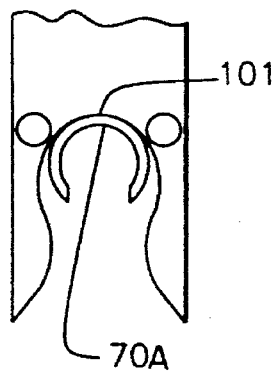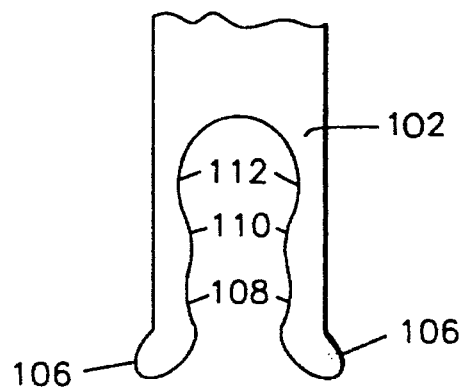
FIG. 6C  FIG. 3B
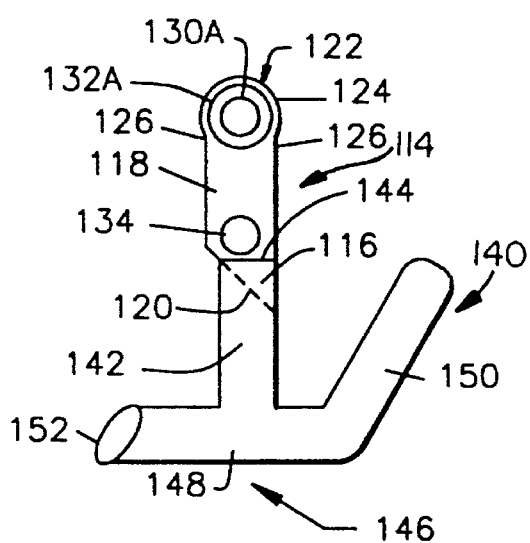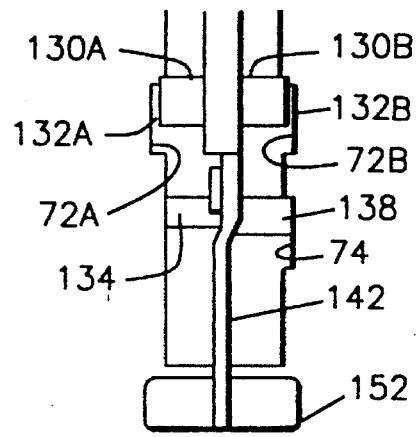
FIG. 4A  FIG. 4B

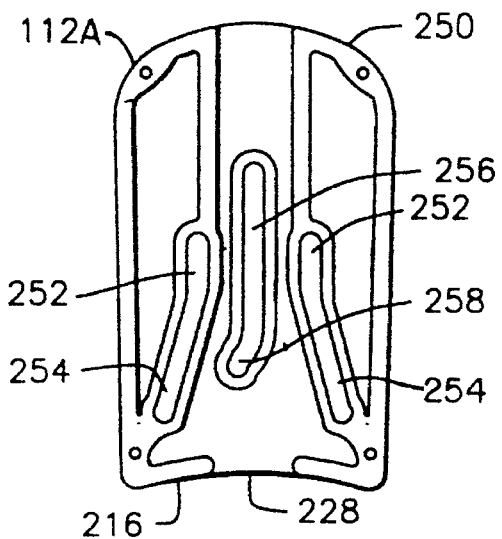
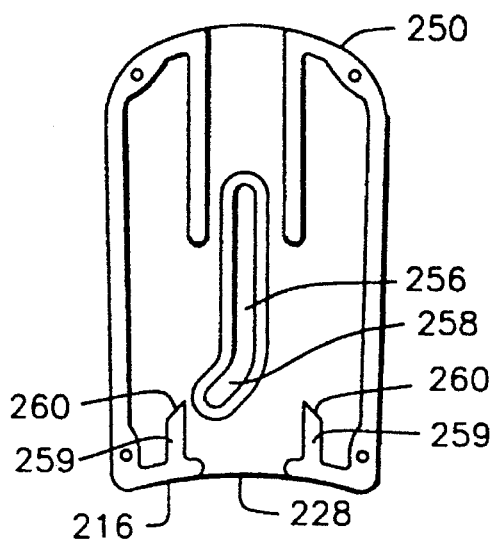
*FIG. 9A*  *FIG. 9B*
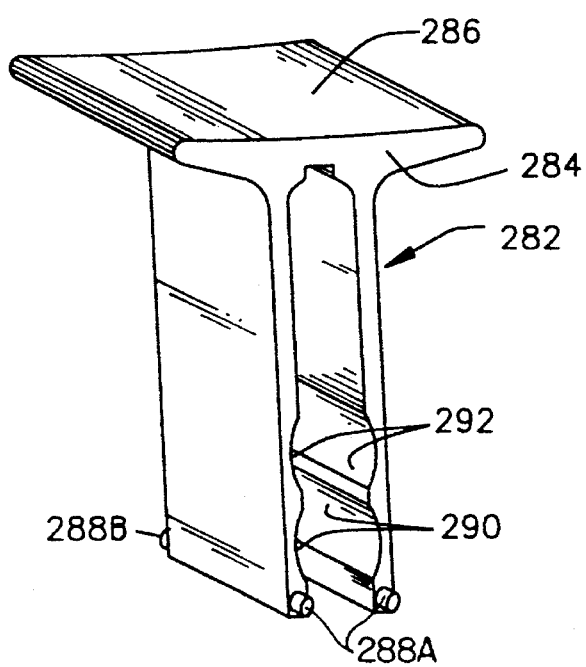
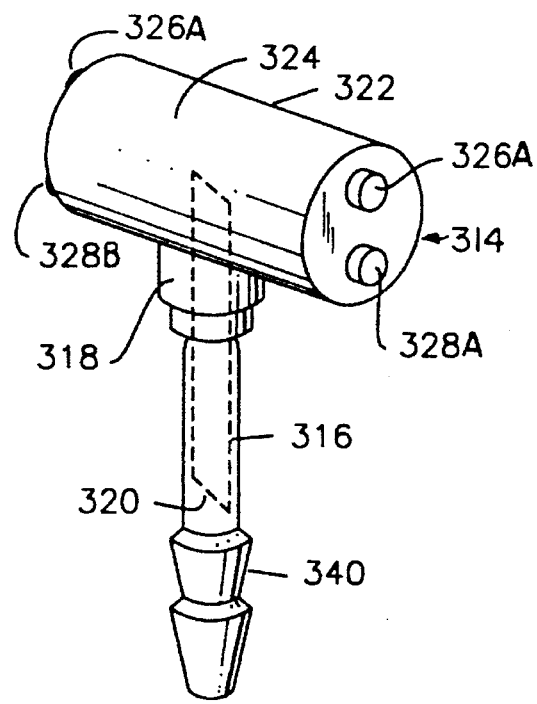
*FIG. 8B*  *FIG. 8C*

SELF ACTIVATED FINGER LANCET

FIELD OF THE INVENTION

This invention relates generally to blood drop generator devices and more particularly to a self activated finger lancet device that creates an incision which corresponds to a cam generated pattern that incises the finger skin of a patient.

BACKGROUND OF THE INVENTION

Blood drop generation devices commonly known as lancets, which are utilized in obtaining blood samples used in performing various blood tests, are well known in the art. These devices operate by creating a small puncture or incision in the patient's skin. Typically, these punctures or incisions are made in the patient's fingertip, although the puncture or incision can be made in other areas of the body such as the foot, arm, or leg.

Prior art lancet devices typically employ a spring loaded cutting blade enclosed within a casing or housing. The person drawing the blood places the housing against the patient's skin and releases the blade with some type of triggering mechanism associated with the device. The potential energy stored within the spring bias of the blade causes the blade to exit the housing and create a puncture or incision in the patient's skin. Accordingly, prior art lancet devices have many advantages including uniform incisions, which can be controlled in terms of location, depth, and sterility. Moreover, because these devices conceal the blade within a housing, the patient is unable to view the often unsettling scene of his or her skin actually being cut. Additionally, many prior art devices include means for retracting the blade back into the housing after the puncture or incision has been made. This feature substantially reduces the danger of spreading disease through contact with the blade. This is an important consideration considering the fact that diseases such as the AIDS virus can be contacted from exposed used blades.

Looking through prior art lancet devices one will discover many different designs which have been developed over the years. The most recent of these designs have retractable blades and other operations that prevent the reuse of the device after a single puncture or incision has been made.

Most prior art lancet devices employ a plunge-type cutting action where the cutting blade is plunged through the skin. The plunge is made perpendicular to the skin so that the size of the puncture generally matches the size of the cutting blade.

An example of a lancet device that creates a plunge-type opening in the skin is shown in U.S. Pat. No. 4,203,446 to Hofert et al. entitled PRECISION SPRING LANCET. Hofert et al. discloses a spring lancet holder which employs means for minimizing the recoil transmitted to the lancet holder by the actuation of the drive mechanism which plunges the lancet into the skin. This is made possible by providing a mass which is caused to move in opposition to the motion of the lancet by a striker spring which is mounted between the lancet and the mass.

In U.S. Pat. No. 4,375,815 issued to Burns entitled RETRACTABLE LANCET ASSEMBLY discloses a lancet device which includes a coil spring positioned inside a housing for maintaining the lancet within the housing when the spring is in a substantially noncompressed state. The housing includes a plurality of elongated openings around its periphery each opening communicating through the side wall of the housing near the lancet. A slidable sleeve is positioned on the outside of the housing and includes a plurality of inwardly projecting feet which are in substantial alignment for projection through the openings in the housing. The feet are adapted to engage the lancet upon movement of the sleeve. This construction causes the spring to become noncompressed and thereby, automatically retracts the point of the lancet back inside the housing. In operation, this design allows the lancet to make a quickly penetrate the skin of the patient and in the same motion quickly retract back into the housing so that it does not dwell for any substantial length of time in the patients finger.

Another automatic retractable lancet assembly is disclosed in U.S. Pat. No. 4,388,925 issued to Burns entitled AUTOMATIC RETRACTABLE LANCET ASSEMBLY. This patent discloses an automatic retractable lancet assembly which comprises a housing with a sharp pointed lancet which is movably mounted therein. An actuating means moves the lancet outwardly from the housing and thereafter becomes disassociated from further movement of the lancet. Means are provided for automatically retracting the lancet back inside the housing.

In U.S. Pat. No. 4,442,836 issued to Meinecke et al. entitled BLOOD LANCET DEVICE discloses a blood lancet device which includes a housing with an exit opening for a lancet guide for guiding the puncturing and retraction of the lancet, a spring drive for the movement of the lancet, and a stop holding the lancet in the position remote from the part of the body from which the blood is to be taken. The exit opening for the lancet includes a release element which functions in connection with the stop.

In U.S. Pat. No. 4,624,253 issued to Burns entitled LANCET, and U.S. Pat. No. 4,677,979 also issued to Burns entitled LANCET a disposable lancet assembly is disclosed which includes integral strategically positioned abutments which serve dual functions. These functions include providing a snap action drive for the lancet and steps for lancet movement control. Also included are integral resilient means on the lance holder body providing a damping of the lancet device or the lancet drive in the puncture direction with automatic withdrawal of the lancet into the housing.

In the U.S. Pat. No. 4,869,249 issued to Crossman et al. a disposable lancet assembly is disclosed that includes a body and a lance with spring means acting between the lance and the body so that in the relaxed condition of the spring, the lance is in a first retracted position within the body. A cap for the body provides a passage through which the lance tip can move and a formation within the cap for engaging the lance in urging it into a second retracted position. Thus, the energizing means as the cap is fitted within body, engages a cap formation which enables the spring means to cause a momentary projection of the lance tip in the passage.

As can be seen, all of these lancets have blade motions which plunge the blade into the skin at an angle which is substantially perpendicular to the skin. It is desirable that the punctures created by these lancets be fairly deep so that good blood flow will result from the puncture. The reason for this is that plunge-type lancet devices typically utilize a pointed blade which creates a V-shaped incision into the patient. The widest region of the puncture is on the surface of the skin wall, the narrowest region coinciding with the point of the puncture. Since the narrowest portion is also the deepest point of the puncture a relatively deep puncture must be made to insure enough capillaries are severed to achieve the necessary bleeding. However, such deep punctures typically are very painful.

It is well known in the art that incisions made by scalpel slices are less painful than punctures made by plunging-type devices. Further, incisions are less intrusive and heal more readily than punctures. Additionally, punctures produced by devices which plunge into the skin subject the skin to forces which damages the skin tissue immediately surrounding the puncture. In contrast, devices which make scalpel like incisions require less downward force and thus, are less harmful to the surrounding skin tissue.

Devices that make scalpel like incisions are exemplified in U.S. Pat. No. 4,643,189 issued to Mintz entitled APPARATUS FOR IMPLEMENTING A STANDARDIZED SKIN INCISION. This device includes a housing having an internal hollow and a base containing an elongated slot. The internal hollow contains a movable pivot arm having a first pivotable end and a second end having a cam follower. There is a cam surface upon which the cam follower of the pivot arm rides. The pivot end of the arm includes a cutting edge which moves transversely while the arm is pivoting. The cam controls the path of the cutting edge as it enters the slot after the unit is triggered, the edge projecting through the slot in the housing along a given path to implement the incision. After traversing the path the cutting edge is withdrawn into the housing to prevent further use and injury.

Another lancet device which creates a scalpel like incision is disclosed in U.S. Pat. No. 5,212,879 entitled METHOD FOR MANUFACTURING A DISPOSABLE RETRACTABLE FIGURE STICK DEVICE, issued to Biro et al. and assigned to International Technidyne Corporation the assignee herein. This patent describes a finger stick device which includes a blade pivot arm having a first end pivotally coupled to a housing and a second end having a upper slope surface and a lower surface. A blade is affixed to the second end such that its cutting edge extends away from the lower surface. A resilient bias member when actuated, traverses the upper surface and depresses the second end of the blade pivot arm such that the blade exits the housing and incises the skin. The incising operation is complete upon the bias member traversing the sloped upper surface of the blade pivot arm.

Still another lancet device which makes a scalpel like incision is disclosed in U.S. Pat. No. 5,314,441 entitled DISPOSABLE LANCET ASSEMBLY, issued to Cusack et al. and assigned to International Technidyne Corporation the assignee herein. In this patent, a lancet device is described which uses a planar blade that implements an incision in the skin of the patient using a slicing action. The blade support arm is pivotally secured within a hollow housing. The pivot connection between the blade support arm and the housing is formed by a pivot pin which extends from the housing and is positioned in a slot receptacle formed on the blade support arm. The pivot pin is free to reciprocally move within the slot receptacle as the blade support arm pivots about the pivot pin. The rotation of the blade support arm about the pivot pin is implemented by a bias spring. The path traversed by the blade support arm as it pivots, is controlled by a groove located around the interior surface of the housing which engages a projection that extends from the blade support arm. Consequently, when the support arm pivots from a first position to a second position, the projection on the blade support arm traverses the groove in the housing, the action of the projection of the blade support arm following the groove in the housing causes the slot receptacle on the blade to reciprocate. This in turn causes the blade to reciprocate within the housing as it rotates with the blade support arm. The blade then exits the housing and implements an incision and is again retracted into the housing traversing a teardrop shaped path.

Although these incisional-type lancet devices have many advantages, a need still exists for easier operating devices which are cheaper to manufacture.

It is, therefore, an object of the present invention to provide an improved disposable self-activated lancet device that utilizes a blade mechanism which moves according to a molded and preset cam generated pattern which incises the finger.

SUMMARY OF THE INVENTION

A self-activated blood drop generator device comprising casing means having an internal hollow and blade means disposed within the hollow of the casing means for generating an incision in a patient's skin. The device includes fork means coupled to the blade means for propelling the blade means through a predetermined path. Cam means associated with the casing means causes the cutting portion of the blade means to travel through an arcuate scalpel-like path as the cutting portion of the blade means passes through an aperture in the casing means. Retractor means associated with the casing means, the blade means and the fork means, are provided for retracting the cutting means of the blade means into the hollow of the casing means. Also provided are accelerator means associated with the casing means for accelerating the fork means through the hollow of the casing means thereby causing the blade means to accelerate through the predetermined path.

The activation of the device causes the cutting portion of the blade means to travel out of the hollow of the casing means through the aperture to incise the patient's skin and then retract back through the aperture into the hollow of the casing means.

BRIEF DESCRIPTION OF THE DRAWINGS

For a detailed understanding of the present invention, reference should be made to the following detailed description taken in conjunction with the accompanying drawings wherein:

FIG. 3B is a front elevational view of the triggering mechanism shown in FIG. 3A without the front outer fork;

FIG. 4A is a front elevational view of the blade assembly;

FIG. 4B is a side elevational view of the blade assembly shown in FIG. 4A;

FIG. 5A is an internal plan view of the device before the removal of the blade protector;

FIGS. 6A–6C illustrate the operation of the outer forks;

FIG. 8B is a perspective view of the triggering mechanism of the second embodiment;

FIG. 8C is a perspective view of the blade assembly of the second embodiment;

FIG. 9A is an internal plan view of the casing section of the device shown in FIG. 8A;

FIG. 9B shows an alternative embodiment of the fork spreading means for the embodiment shown in FIG. 9A.

DETAILED DESCRIPTION OF THE INVENTION

Figure 1A:
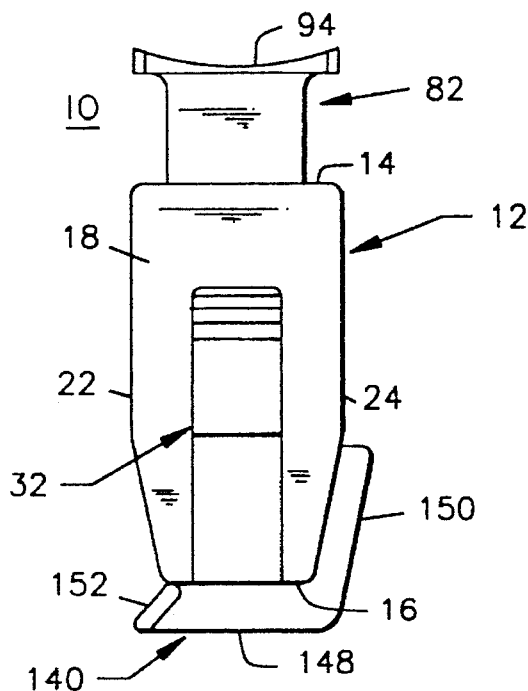
FIG. 1A shows a front elevational view of the self-activated finger lancet device 10 of the present invention.

Referring to FIG. 1A there is shown a front elevational view of the self-activated finger lancet device 10 of the present invention. The device 10 is a true incisional-type blood drop generator as the motion of the blade is controlled by a cam pattern that causes a blade motion which incises the user's finger in a scalpel-like manner as will be explained below.

As can be seen in FIG. 1A, the device 10 has three basic components consisting of a casing 12, a blade assembly 114, and a triggering mechanism 82. The casing 12 of the device 10 is molded from a suitable plastic and has a generally rectangular-shaped upper casing portion which extends down to a tapered lower casing portion. The casing 12 includes a top wall 14, a bottom wall 16, a front wall 18, a rear wall 20 (not visible), a first side wall 22, and second side wall 24. The shape of the casing 12 shown in FIG. 1A makes the device 10 easy to grip and operate. It should be understood, however, that the casing 12 of the device 10 can be any other suitable shape that makes the device 10 easy grip and operate. The case shape plays little role when the device is used as a self-lancet device. However, when the device is used by a health care professional on a patient, the side notches provide a secure gripping feature for the index and third finger of one operators hand permitting the thumb to engage and activate the trigger button.

The casing 12 of the device 10 houses the triggering mechanism 82 a portion of which extends out of the interior of the casing through an aperture 26 (not visible) in the top wall 14 thereof. The exposed end portion of the triggering mechanism 82 terminates in a concave-shaped trigger button 94 which easily accommodates a user's thumb.

The casing 12 further houses the blade assembly 114. The blade assembly 114 includes a blade protector 140 the lower portion of which extends out of the interior of the casing 12 through a slot 28 (not visible) in the bottom wall 16 of the casing 12. Although it is not visible in FIG. 1A, the upper portion of the blade protector 140 is frangibly connected to a blade holder portion 118 of the blade assembly 114 as will be described later on. The lower portion of the blade protector 140 is formed as a bent cantilever 146 that has a horizontal portion 148 which merges into a vertical portion 150. The horizontal portion 148 traverses the bottom wall 16 of the casing 12 between the first side wall 22 and the second side wall 24. The vertical portion 150 generally follows the tapered profile of the second side wall 24 as it-extends up along the lower portion of the casing 12. A finger push tab 152 is disposed at the free end of the horizontal portion adjacent the first side wall 22 of the casing 12. The push tab 152 extends perpendicularly relative to the horizontal portion 148 between the front and rear walls of the casing and is angled slightly such that the face of the tab 152 points up and away from the first side wall of the casing. The structure of the lower portion of the blade protector 140 enables the user to easily detach the blade protector 140 from the blade assembly 114 prior to use as will be explained.

A safety lock assembly 32 for locking the blade assembly to prevent inadvertent operation of the device 10, is hinged to lower portion of the front wall 18 of the casing 12. The safety lock assembly 32 includes an arm portion 34, one end of which is hinged to the front wall 18 of the casing 12 to enable the safety lock assembly 32 to pivot. The other end of the arm portion 34 merges into a button portion 36. Preferably, the front surface of the button member is fluted 38 as shown to provide easy gripping by a user's finger.

Figure 1B:
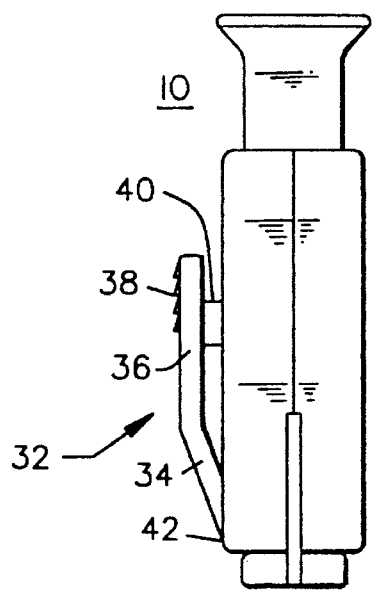
FIG. 1B is a side elevational view of the device shown in FIG. 1A.

In the side elevational view of FIG. 1B, the lock assembly 32 described above can be better understood. As can be seen, the arm portion 34 extends up and away from its attachment point 42 at the front wall 18 of the casing 12. This arrangement spaces the button portion 36 away from the front wall 18 of the casing 12 in an unlocked position. A cylindrical projection 40 extends perpendicularly away from the rear surface of the button portion 36 and partially enters an aperture 44 (not visible) in the front wall 18 of the casing 12. The aperture 44 in the front wall 18 of the casing 12 communicates with a portion of the blade assembly housed within the casing 12. Accordingly, when the button portion 36 is pressed to activate the safety lock assembly 32, the arm portion 34 pivots the button portion 36 towards the front wall 18 of the casing 12. As this occurs, the cylindrical projection 40 on the rear surface of the button portion 36 travels entirely through the aperture 44 in the front wall 18 into the interior of the casing 12 and locks the blade assembly 32 to prevent inadvertent operation of the device 10. This is especially useful when the blade protector is being removed as will be described later on in greater detail. The hinge 42 or junction where the arm portion 34 is pivotally attached to the front wall 18 is a unitarily formed living hinge which biases the safety lock assembly 32 in the unlocked position. It should be understood, however, that any other suitable well known biased hinge arrangement can be employed if desired. In any case, when the button portion 36 is released, the bias applied by the hinge 42 pivots the safety lock assembly 32 away from the front wall 18 and thereby returns the button portion 36 to the unlocked position.

FIG. 1B also illustrates that the casing 12 is comprised of a front casing section 12A and a rear casing section 12B that are secured together as will be explained shortly.

Figure 1C:
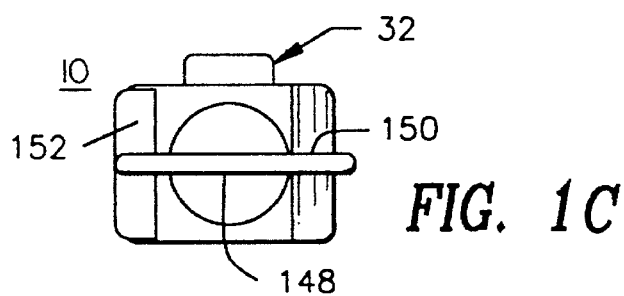
FIG. 1C is a bottom view of the device shown in FIG. 1A.

FIG. 1C is a bottom view of the device shown in FIG. 1A and illustrates a concave recess 30 defined in the bottom wall 16 of the casing 12 that is provided to intimately receive the curved surface of a user's finger tip.

Figure 1D:
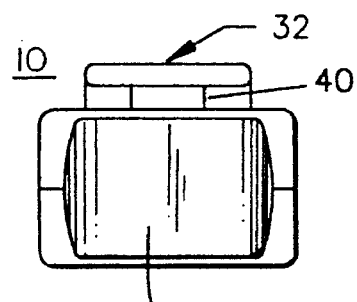
FIG. 1D is a top view of the device shown in FIG. 1A.

FIG. 1D is a top view of the device 10 shown in FIG. 1A and illustrates the concave surface of the trigger button. The cylindrical projection 40 and the button portion 36 of the safety lock assembly 32 are also visible in this figure.

Figure 1E:
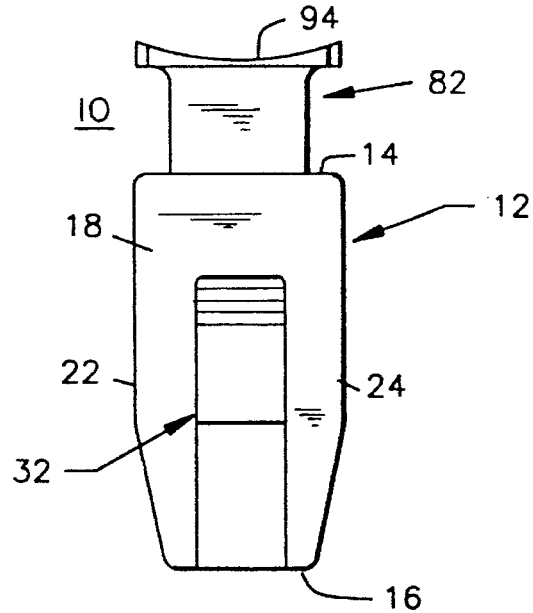
FIG. 1E is a front elevational view of the device shown in FIG. 1A after the blade protector has been removed.

FIG. 1E is a front elevational view of the device 10 of FIG. 1A after the blade protector has been removed.

Figure 1F:
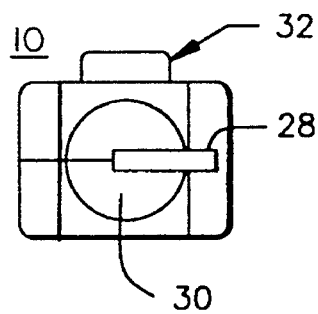
FIG. 1F is a bottom view of the device shown in FIG. 1E.

FIG. 1F is a bottom view of the device of FIG. 1E. As can be seen, removal of the blade protector enables one to view the slot 28 in the bottom wall 16 of the casing 12. Note that one end of the slot 28 extends partially into the second side wall 24 of the casing 12 the purpose of which will be explained later.

Figure 2A:
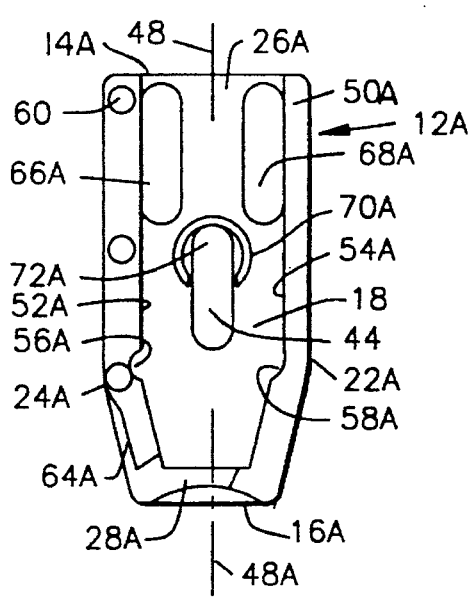
FIG. 2A is an internal plan view of the front casing section.

Referring to FIG. 2A, there is shown an internal plan view of the front casing section 12A. As can be seen, the front casing section 12A includes the front wall 18 of the casing 12. Preferably, all of the features of the front casing section 12A are molded with the front wall 18 as a single unitary part. However, it is possible to separately attach or machine these features to or in the front wall 18 of the front casing section 12A if desired. In any case, the front casing section 12A defines a vertical axis 48A. An outer peripheral flange 50A extends along the interior peripheral surface of the front wall 18. The outer peripheral flange 50A forms first and second side walls halves 22A, 24A; a bottom wall half 16A; and a top wall half 14A of the casing 12. The gap in outer peripheral flange 50A defines aperture half 26A. The inner surfaces of the first and second side wall halves 22A and 24A form inner fork guide surfaces 52A, 54A (in conjunction with similar surfaces in the rear casing section 12B) for the triggering mechanism 82. Undercuts 56A and 58A are respectively located at the marginal lower end of each inner surface. The inner fork guide surfaces 52A, 54A and the under-cuts 56A and 58A formed therein coact with the triggering mechanism 82 as will be explained later on. A series of apertures 60 are defined in the outer peripheral flange 50A and accommodate extending rods associated with the rear casing section 12B to allow the two casing sections to be coupled together. The bottom wall half 16A includes slot half 28A and concave recess half 30A. Looking carefully, one can see that the slot half 28A communicates with the interior of the front casing section 12A. However, a portion of this slot half 28A also merges into the second side wall half 24A as earlier described. This portion of the slot half 28A does not communicate with the interior of the front casing section 12A because the outer peripheral flange 50A is not fully relieved in this area and thereby forms abutment half 64A. The abutment half 64A (in conjunction with a similar structure on the rear casing section 12B) coacts with the vertical portion of the cantilever to enable the blade protector to be removed as will be explained in greater detail. A first pair of spaced apart triggering mechanism guide grooves 66A and 68A are defined in the interior surface of the front wall 18 and extend in the direction of the vertical axis 48A. A C-shaped fork spreading projection 70A is located between and immediately below the triggering mechanism guide grooves 66A and 68A. Extending from within the C-shaped fork spreading projection 70A in the direction of the vertical axis 48 A is a first blade holder guide groove 72A. The earlier described aperture 44 in the front wall 18 extends into the lower portion of the first blade holder guide groove 72A.

Figure 2C:
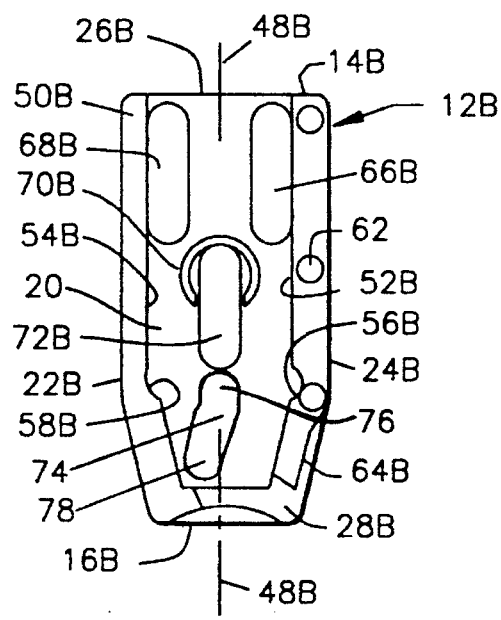
FIG. 2C is an internal plan view of the rear casing section.
Figure 2B:
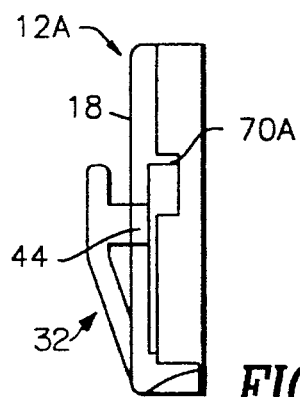
FIG. 2B is a cross-sectional view of the casing section shown in FIG. 2A.

FIG. 2B shows a cross-sectional view of the front casing section 12A of FIG. 2A through line 2B—2B. The fork spreading projection 70A can be easily seen in this figure. The aperture 44 in the front wall 18 and the safety lock assembly 32 are also clearly visible.

FIG. 2C, shows an internal plan view of the rear casing section 12B. As can be seen, the rear casing section 12B includes the rear wall 20 of the casing 12. Preferably, all of the features of the rear casing section 12B are molded with the rear wall 20 as a single unitary part just as was described with respect to the front casing section 12A. Likewise, it is possible to separately attached or machine these features to or in the rear wall 20 if desired. In any case, the rear casing section 12B defines a vertical axis 48B. An outer peripheral flange 50B extends along the interior peripheral surface of the rear wall 20. The outer peripheral flange 50B forms first and second side walls halves 22B and 24; a bottom wall half 16B, and a top wall half 14B. The second half 26B of the earlier described aperture 26 is defined in the top wall half 14 B. The inner surfaces of the first and second side wall halves 22B and 24B form inner fork guide surfaces 52B, 54B. Undercuts 56B and 58B are respectively located at the marginal lower end of each inner surface. A series of rods 62 extend from the outer peripheral flange 50B and are received by the apertures 60 in the front casing section 12A as earlier described. The bottom wall half 16B defines a slot half 28B and a concave recess half 30B. The slot half 28B and abutment half 30B are formed in the outer peripheral 50B in the same manner as described above with respect to the front casing section 12A. A pair of spaced apart triggering mechanism guide grooves 66B and 68B are defined in the interior surface of the rear wall 20. A second C-shaped fork spreading projection 70B is located between and immediately below the trigger guide grooves 66B and 68B. Extending from within the C-shaped fork spreading projection 70B is a second blade holder guide groove 72B. Immediately below the blade holder guide groove 72B is a cam groove 74. The cam groove 74 includes an upper portion 76 which extends in the same direction as the vertical axis 48B. The upper portion 76 of the cam groove 74 merges into a lower portion 78. The lower portion 78 of the cam groove 74 extends in a direction toward the first side wall 22 and controls the movement of the blade assembly when the device 10 is activated as will be explained shortly.

Figure 2D:
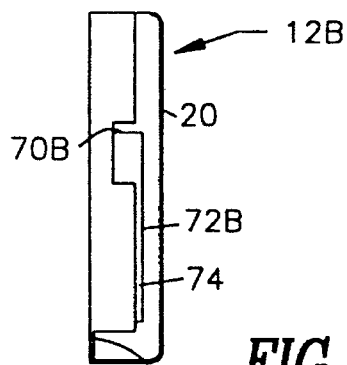
FIG. 2D is a cross-sectional view of the casing section shown in FIG. 2D.

FIG. 2D depicts a cross-sectional view of the rear casing section 12B of FIG. 2C through line 2D—2D and illustrates the structure of the fork spreading projection 70B, the blade guide groove 72B and the cam groove 74.

Figure 2E:
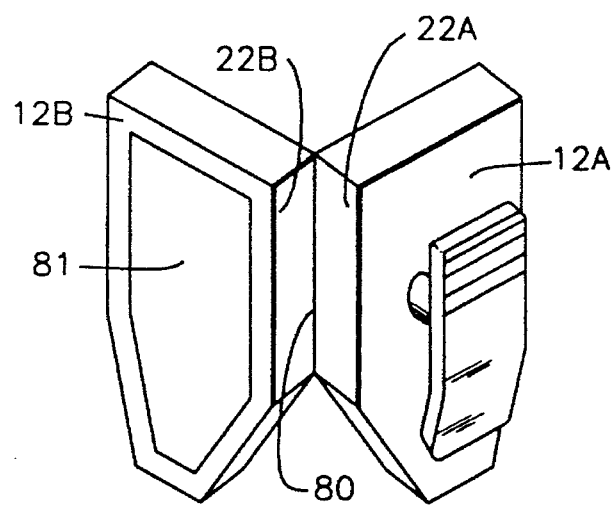
FIG. 2E is a perspective view of the casing sections.

Since both of the casing sections are to be molded from plastic it is contemplated that the sections be molded as one part hinged together at the first side wall halves 22A and 22B by a unitarily formed living hinge 80 as shown in FIG. 2E. The exterior surface of the rear casing section 12B is shown with an indentation 81 for receiving identifying indicia or the like.

Figure 3A:
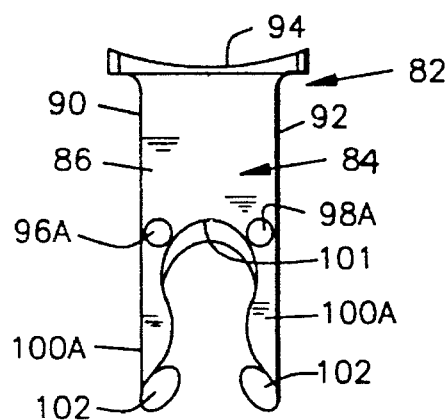
FIG. 3A is a front elevational view of the triggering mechanism.

Referring to FIG. 3A, there is shown a front elevational view of the triggering mechanism 82. The triggering mechanism 82 comprises a trigger body 84. In the preferred embodiment shown in FIG. 3A, the trigger body 84 includes a front surface 86, a rear surface 88 (not visible), a first side surface 90, and second side surface 92. Disposed at the upper end of the trigger body is the concave-shaped trigger button 94. A first pair of cylindrical-shaped triggering mechanism guide groove followers 96A and 98A project from the front surface 86 of the trigger body 84. The first pair of guide groove followers 96A and 98A ride and follow respective triggering mechanism guide grooves 66A and 68A in the front wall 18 of the front casing section 12A. A second pair of cylindrical-shaped triggering mechanism guide groove followers 96B and 98B project from the rear surface 88 of the trigger body 84 (not visible). The second pair of guide groove followers 96B and 98B ride and follow respective triggering mechanism guide grooves 66B and 68B in the rear wall 20 of the rear casing section 12B. The trigger guide grooves/followers enable the triggering mechanism 82 to be smoothly pressed into the casing 12 in a precise manner. This enhances the tactile feel of the triggering mechanism 82. Depending from the lower portion of the trigger body 84 is a resilient front outer fork 100A, a resilient rear outer fork 100B (only the front outer fork is visible) separated by a resilient inner fork 102 which extends down beyond the two outer forks. Each outer fork includes an arcuate fork stop 101 and a pair of inwardly facing cams 104. The inwardly facing cams 104 on each of the outer forks coact with their respective fork spreading projection 70A, 70B of the casing 12 to accelerate the downward movement of the triggering mechanism 82.

FIG. 3B shows the inner fork 102 separate from the outer forks 100A and 100B. The inner fork 102 includes a pair of outwardly facing cam surfaces 106 at the ends of the fork inner fork 102. A first pair of concave inner surfaces 108 are defined just above the outwardly facing cam surfaces 106. The first pair of concave inner surfaces 108 merge into a pair of inwardly facing cam surfaces 110. Continuing further up along the inner fork 102, the inwardly facing cam surfaces 110 merge into a second pair of concave inner surfaces 112.

The triggering mechanism 82 is preferably, a unitarily molded assembly made from a suitable plastic. It should be understood, however, that the outer forks 100A and 100B can be molded separately from the trigger body 84 and later assembled together.

Figure 3C:
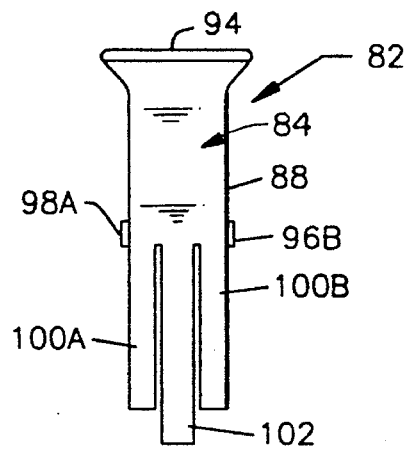
FIG. 3C is a side elevational view of the triggering mechanism shown in FIG. 3A.

FIG. 3C shows a side elevational view of the triggering mechanism 82 of FIG. 3A. In this view, the second pair of triggering mechanism guide groove followers 96B and 98B can be seen extending from the rear surface of the trigger body 84.

Referring to FIG. 4A, there is shown a front elevational view of the blade assembly 114. The blade assembly 114 includes a blade 116 and a blade holder 118. The blade 116, shown by broken lines, is scalpel-like in appearance and function and includes a blade cutting edge 120. The blade 116 is preferably a stamped full hard stainless steel 301 or 304 series blade, secondarily ground in a 0.006 thick or 0.003 thick version for improved sharpness and painless incising. The blade 116 is inset molded using a suitable plastic and fully encapsulated into the blade holder 118 except for approximately two locating points (not shown). Inset molding of blades into blade holders is well known in the art and needn't be describe here. The upper portion of the blade holder 118 includes an enlarged section 122 having a convex outer surface 124 which is adapted to be received by the first and second pairs of concave inner surfaces 108 and 112 defined by the inner fork 102 of the triggering mechanism 82. A pair of reliefs 126 are formed where the convex outer surface 124 of the upper enlarged section 122 merges into an intermediate section of the blade holder 128. Cylindrical-shaped spacer members 130A and 130B extend from each of the front and rear faces of the enlarged section 122 of the blade holder 118. Cylindrical-shaped blade holder guide groove followers 132A and 132B coaxially extend from each respective spacer member 130A and 130B. A cylindrical-shaped thrust spacer 134 extends from front face of the lower section 136 of the blade holder 118. A cylindrical-shaped cam groove follower 138 (see FIG. 4B) extends from the rear face of the blade holder 118 opposite the thrust spacer 134. The blade protector 140, described earlier, depends from the lower section 136 of the blade holder 118. The blade protector 140 includes a cover member 142 which is unitarily formed with the portion of the blade protector 140 that forms the cantilever 146. The upper portion of the cover member 142 encapsulates the cutting edge 120 of the blade 116 and is frangibly connected to the lower section of the blade holder by a membrane 144 or like frangible element.

FIG. 4B shows a side elevational view of the blade assembly 114 of FIG. 4A assembled in the casing 12 of the device 10. As can be seen the spacer members 130A and 130B position the blade assembly 114 centrally between the front and rear casing sections 12A and 12B so that the enlarged section 122 is coupled with the inner fork 102 of the triggering mechanism 82. The blade holder guide groove followers 132A and 132B ride in respective blade holder guide grooves 72A and 72B of the casing sections. The thrust spacer 134 engages the interior surface of the front wall 18 to hold the cam groove follower 138 in the cam groove 74 in the rear wall 20 of the casing 12 as the blade assembly 114 reciprocates in the casing 12 when the device 10 is activated.

Figure 5B:
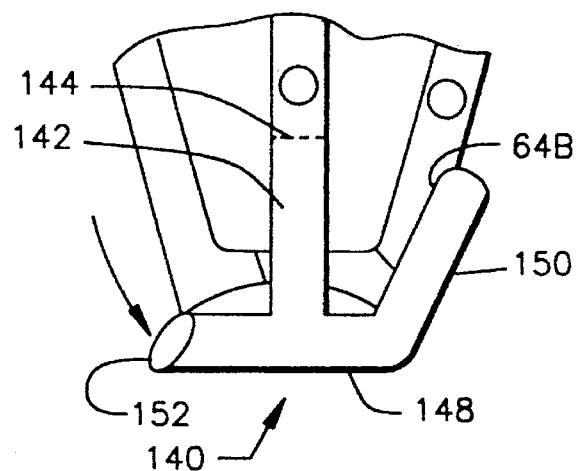
FIGS. 5B and 5C illustrate the removal the blade protector.
Figure 5C:
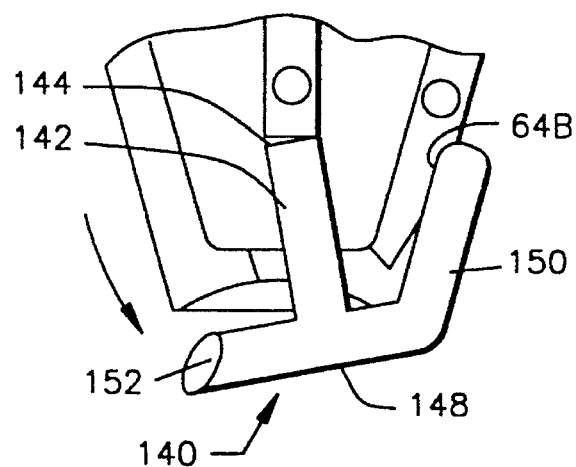

The discussion which follows describes the operation of the device 10. FIG. 5A is an internal plan view of the device 10 before removal of the blade protector 140. The device 10 shown therein is armed and requires no cocking since the incision and operating force is generated by the user. In order to use the device 10 the user must first remove the blade protector 140 of the blade assembly 114. To accomplish this, the user grips the casing 12 in one hand and presses the safety lock button 36 with one of the fingers of that hand to lock the blade assembly 114 in the casing 12. The user then uses one or two fingers of the other hand to press the finger push tab 152 to break-off the blade protector 140 as can be seen in FIG. 5B. As the user applies force to the finger push tab 152, the vertical portion 150 of the cantilever 146 abuts with the abutments 64A and 64B defined by the casing sections (only the abutment 64B of rear casing section 12B is shown) and acts as a lever to fracture the membrane 144 where the blade protector 140 and the remaining portion of the blade assembly 114 are attached. As the membrane 144 fractures, the blade protector 140 rotates as shown in FIG. 5C, and pulls away from the blade assembly 114 so that it can be removed through the slot in the casing.

Once the blade protector 140 has been removed, the device 10 is ready to be used. The finger to be incised is prepared according to established medical procedure and the device 10 is positioned so that the concave surface 30 in the bottom wall 16 of the casing 12 comfortably engages the finger to be incised. The concave surface of the trigger button 94 is engaged by the thumb of the same hand. Accordingly, the device 10 is gripped between the finger to be incised and the thumb of the same hand. The thumb and the finger are then thrust together to activate the device 10.

Figure 6A:
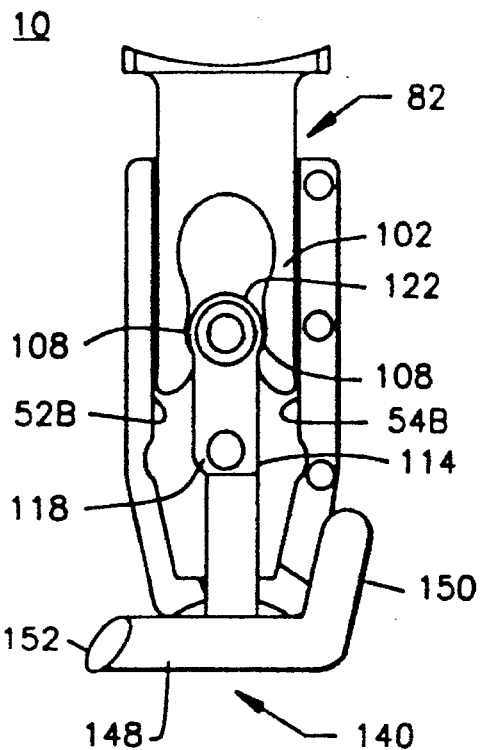

FIGS. 6A–6C, illustrate how the cams on the front outer fork 100A coact with the first fork 70A spreading projection on the front wall 18 of the casing 12 when the device 10 is activated. The discussion which follows applies equally to the rear outer fork 100B and second fork spreading projection 70B. Accordingly, when the user presses down the triggering mechanism 82 to activate the device 10, a leading surface of each inwardly facing cam 104 on the outer fork 100A engages the convex surface of the fork spreading projection 70A thereby causing an opposing force which creates a slight resistance as shown in FIG. 6A. The user must apply a sufficient amount of trigger pressure to overcome this resistance. The trigger pressure causes the front outer fork 100A to spread and flex over the surface of the fork spreading projection 70A creating a spring bias force. As this occurs the inwardly facing cams 104 move along the surface of the fork spreading projection 70A. When the surface of the fork spreading projection 70A contacts the high point surface 105 on each cam 104 as shown in FIG. 6B, the front outer fork 100A becomes fully spread which results in a maximum buildup of spring bias force. As the cams 104 slide further past the fork spreading projection 70A the spring bias force stored in the front outer fork 100A causes the front outer fork 100A to suddenly close and return to its original shape. When this occurs the triggering mechanism 82, which is also coupled to the blade assembly 114, accelerates down into the casing 12. The downward travel of the triggering mechanism is halted when the arcuate stop 101 of the front outer fork 100A engages the fork spreading projection 70A as shown in FIG. 6C.

Figure 7A:
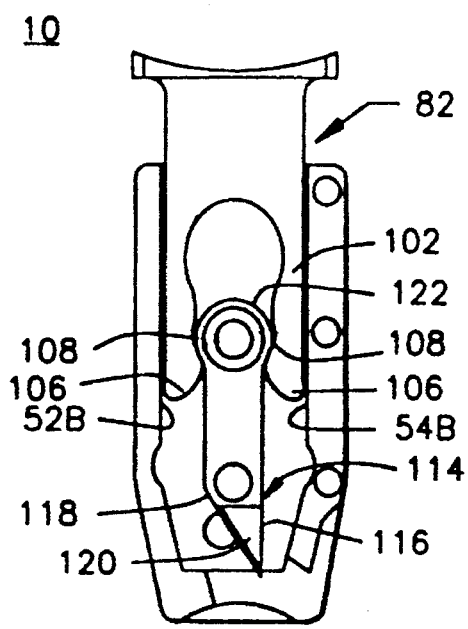
FIGS. 7A–7D illustrate the operation of the inner fork and the blade assembly.
Figure 7B:
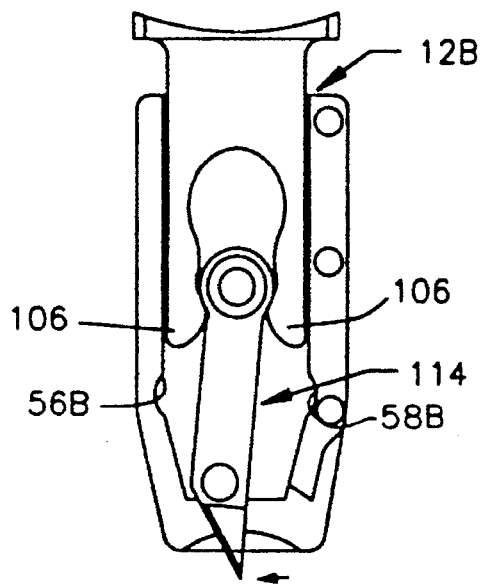
Figure 7C:
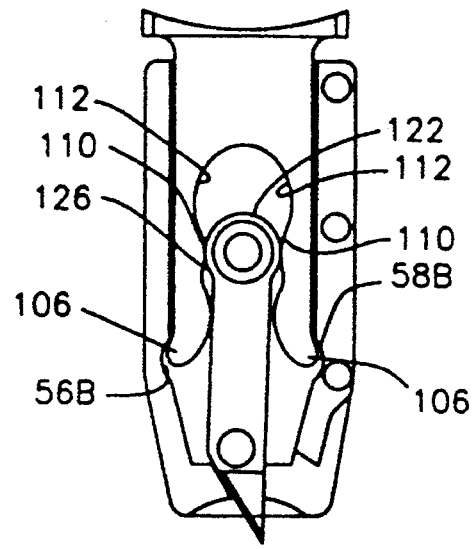
Figure 7D:
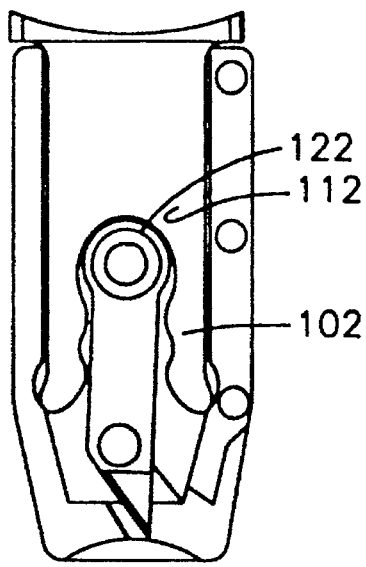

FIGS. 7A–7D, illustrate how the blade assembly 114 operates in conjunction with the triggering mechanism 82 when the device 10 is activated. FIG. 7A is an internal view of the device 10 immediately after the activation of the device 10 which shows the enlarged section 122 of the blade assembly residing within the first pair of concave inner surfaces 108 of the inner fork 102. As the user presses down the trigger assembly 82, the outwardly facing cam surfaces 106 of the inner fork 102 ride along the inner guide surfaces 52B and 54B defined by respective casing sections 12A and 12B (only the rear casing section 12B and its structures are shown for ease of illustration). In FIG. 7B, as the triggering assembly 82 accelerates the blade assembly 114 in a downward stroke through the casing, the lower portion of the blade holder 118 pivots as it follows the cam guide groove 74 via the cam guide groove follower 138. This causes the cutting edge 120 of the blade 116 to enter the skin of the finger to be incised in a scalpel-manner such that an incision, having a depth of approximately 0.094 inches and a length of 0.063 inches, is made in the skin. The completion of the incision marks the end of the blade assembly's 114 downward stroke. However, the triggering mechanism 82 continues to travel down through the casing 12 whereby the outwardly facing cam surfaces 106 of the inner fork to enter the under-cut portions 56B and 58B defined by the rear casing section 12B as shown in FIG. 7C. This enables the inner fork 102 to spread slightly. As the triggering mechanism 82 continues to move down, the enlarged section 122 of the blade assembly 114 rides up between the inwardly facing cam surfaces 110 of the inner fork 102 and spreads the inner fork 102 thereby causing an opposing force which creates a spring bias. This initiates retraction of the blade assembly 114. As the enlarged section 122 of the blade assembly 114 moves slightly past the high point of the inwardly facing cam surfaces 110, the cam surfaces 110 slide onto the reliefs 126 on the enlarged section 122. The reliefs 126 allow spring bias stored in the inner fork 102 to suddenly close the inner fork 102 and return to its original shape. As the inner fork 102 closes it accelerates the enlarged section 122 of the blade assembly into the second pair of concave inner surfaces 112 to retract the blade assembly 114 including the blade 116 into the casing 12 as shown in FIG. 7D. The blade is now out reach and cannot be touched or used again to cut. Accordingly, the device 10 can now be safely disposed of.

Figure 8A:
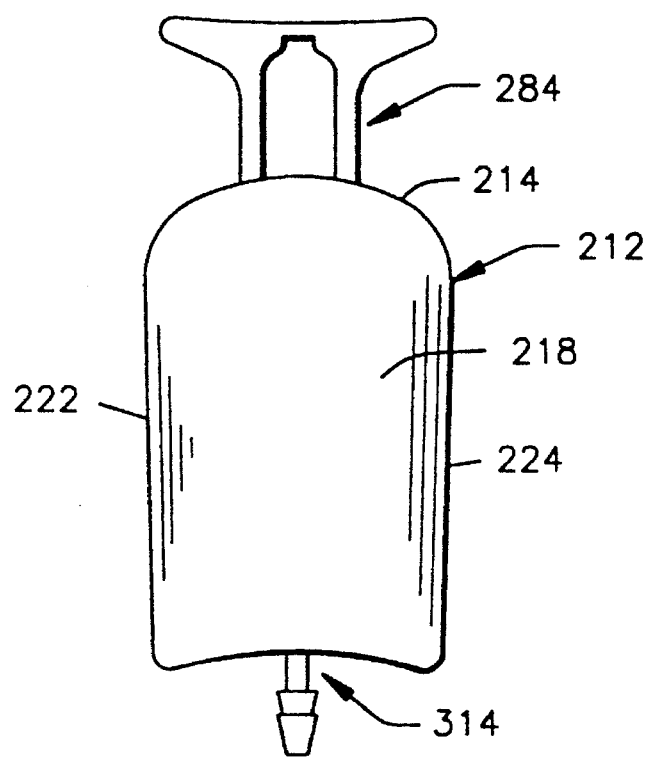
FIG. 8A is a front elevational view of a second embodiment of the present invention.

FIG. 8A, is a front elevational view of a second preferred embodiment of the present invention designated by the numeral 210. The device 210 of FIG. 8 also includes a two section casing 212 (only the front section is visible), a blade assembly 314, and a triggering mechanism 282. The casing 212 of the device 210 is molded from a suitable plastic. The casing 212 includes a top wall 214, a bottom wall 216, a front wall 218, a rear wall 220 (not visible), a first side wall 222, and second side wall 224.

FIG. 8B shows a perspective view of the triggering mechanism 282. The triggering mechanism 282 comprises a fork body 284. Disposed at the upper end of the fork body is the concave-shaped trigger button 286. Two pairs of cylindrical-shaped triggering mechanism channel followers 288A and 288B project from the front and rear surfaces of the trigger body 284 adjacent the end portions of the fork body 284. A first pair of inner concave recesses 290 are defined just above the channel followers 288A and 288B. Moving up along the fork body 284 are a second pair of inner concave recesses 292.

FIG. 8C shows the blade assembly 314 which includes a blade protector 340 which extends out of the interior of the casing 212 through an aperture 228 the bottom wall 216 of the casing 212. The upper portion of the blade protector is frangibly connected to a blade holder portion of the blade assembly in the same manner as previously described with regard to the first embodiment. The blade 316, shown by broken lines, includes a blade cutting edge 320. The blade 316 is inset molded using a suitable plastic and fully encapsulated into the blade holder 318. The upper portion of the blade holder 318 includes a cylindrical-shaped spacer section 322 having a convex outer surface 324 which is adapted to be respectively received by the first and second pairs of concave inner recesses 290 and 292 defined by the fork body 284 of the triggering mechanism 282. An upper pair of opposing blade holder cam channel followers 326A and 326B extend from each side of the spacer section 322 on the upper portion thereof. A lower pair of opposing cylindrical-shaped of opposing cam channel followers 328A and 328B extend from the spacer section 322 on a lower portion thereof.

FIG. 9A shows an internal plan view of the front casing section 212A of the device 210 shown in FIG. 8A. In the second embodiment, the front casing section 212A and rear casing section 212B are mirror images of each other. Thus, the following description of the internal features of front casing section 212A equally applies to the internal features of the rear casing section 212B.

In any case, the front casing section 212A includes an outer peripheral flange 250 which in conjunction with a similar structure on the rear casing section, defines the top, bottom and side walls of the casing 212. A pair of fork guide channels 252 extend along the axis 248 of the front casing section 212A. Each fork guide channel 252 merges into a fork spreading dog-leg shaped channel portion 254. The channel followers of the triggering mechanism ride and follow the fork guide and spreading channels in the casing sections. Located between the fork guide channels 252 and the fork spreading channels 254 is a cam channel 256. The lower end 258 of the cam channel 256 forms a dog-leg. The upper and lower pair of cam channel followers 326A, 326B, 328A, and 328B ride and follow their respective cam channels in the front and rear casing sections. When the lower pair of cam channel followers 328A and 328B enter the dog-leg portion of their respective cam channel, the lower portion of the blade holder 314 pivots. This causes the cutting edge 320 of the blade 316 to enter the skin of the finger to be incised in a scalpel-manner similar to as was described with respect to the first embodiment.

FIG. 9B shows an alternative the fork spreading means which takes the form of a pair of fork spreading projections 258 extending up from the bottom wall 216 of the casing 212. The fork spreading projections 259 include outwardly facing inclined surfaces 260 which engage corresponding inwardly facing inclined surfaces (not shown) defined at the ends of the fork body 284. The inclined surfaces on the ends of the fork body would eliminate the need for the channel followers.

Figure 10A:
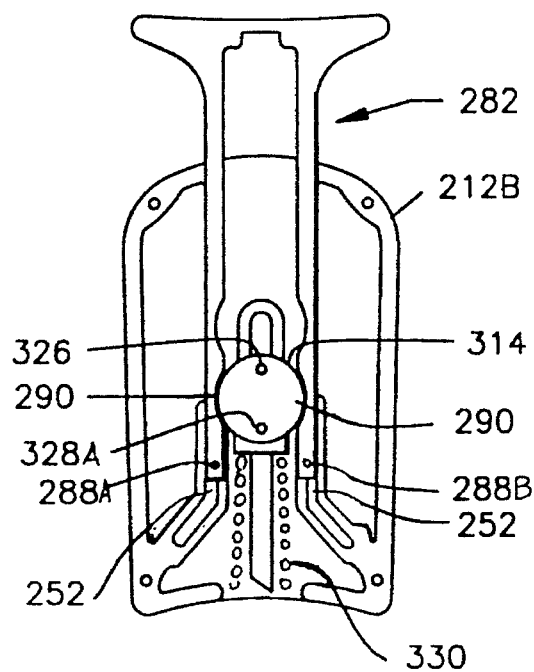
FIGS. 10A–10D illustrate the operation of the device of FIG 8A.

FIGS. 10A–10D illustrate how the triggering mechanism 282 and the blade assembly 314 operate when the device 210 is activated. Only the rear casing section 212B is shown for the sake of clarity. FIG. 10A is an internal view of the device 210 immediately after being activated. Notice that the spacer section 322 of the blade assembly 314 is positioned in the first pair of concave recesses 290. As the user presses down the triggering assembly 282 and compresses the reversing spring 330, the channel followers 288A and 288B on the fork body follow the fork guide channels 252. At the same time, the cam channel followers 326A and 328B of the blade assembly follow the path of the upper portions of the cam channels 256 (not visible).

Figure 10B:
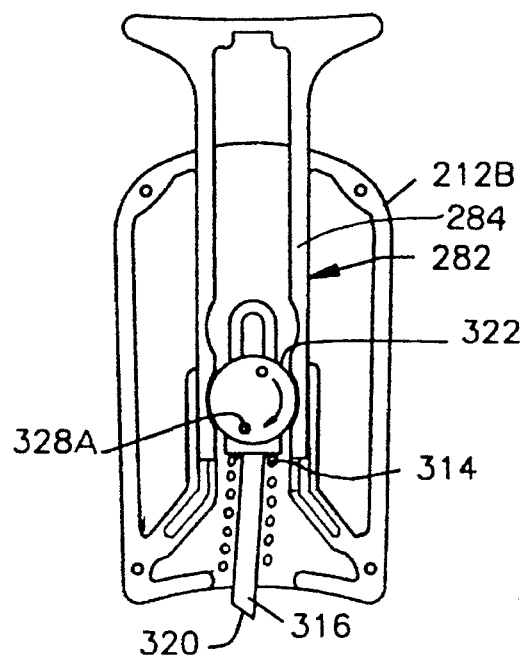
Figure 10C:
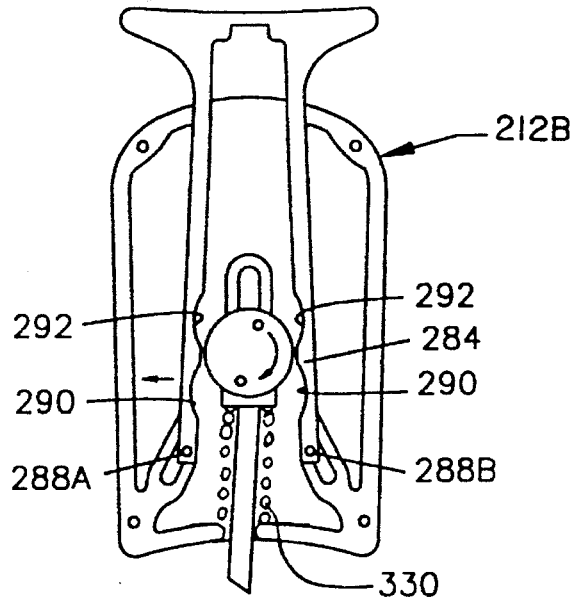
Figure 10D:
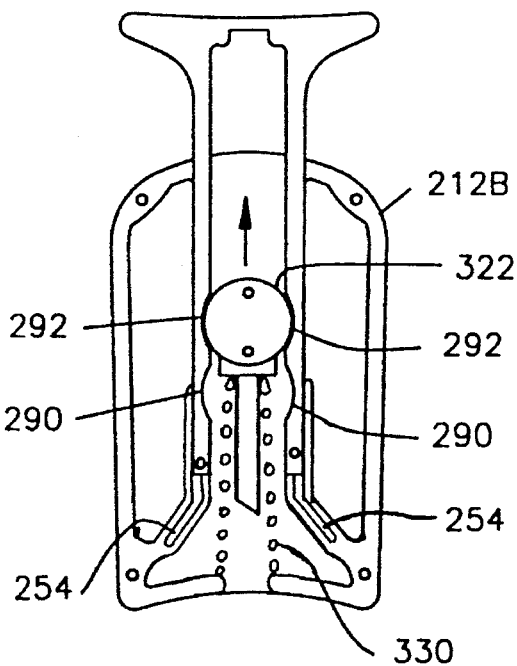

FIG. 10B, shows the lower portion of the blade holder 314 pivoting as it follows the cam channels 256 (not visible) via the cam channel followers, which causes the cutting edge 320 of the blade 316 to enter the skin of the finger to be incised in a scalpel-manner. The completion of the incision marks the end of the blade assembly's 314 downward stroke. However, the triggering mechanism 282 continues to travel down through the casing 212 where the followers on the fork body 284 enter the dog-leg shape fork spreading channel 254 which spreads the fork body 284 as shown in FIG. 10C. This initiates retraction of the blade assembly 314. Accordingly, the reversing spring 330, which is now fully compressed, forces the spacer section 322 of the blade assembly 314 up into the second pair of concave inner recesses 292 where the blade assembly 314 including the blade 316 is now fully retracted into the casing 212 as shown in FIG. 10D.

It should be understood that the embodiments described herein are merely exemplary and that a person skilled in the art may make many variations and modifications to these embodiments utilizing functionally equivalent elements to those described herein. Any and all such variations or modifications as well as others which may become apparent to those skilled in the art, are intended to be included within the scope of the invention as defined by the appended claims.

We claim:

1. A self-activated blood drop generator device comprising:

casing means having an internal hollow;

blade means disposed within said hollow of said casing means for generating an incision in a patient's skin, wherein upon the activation of said device, said blade means follows a predetermined path which causes a cutting portion of said blade means to travel out of said hollow of said casing means through an aperture defined in an end of said casing means to incise the patient's skin and then retract back through said aperture into said hollow of said casing means;

fork means coupled to said blade means for propelling said blade means through said predetermined path;

cam means associated with said casing means for causing said cutting portion of said blade means to travel through an arcuate scalpel-like path as said cutting portion of said blade means passes through said aperture in said casing means, wherein said cam means includes a cam groove defined in an interior surface of said casing means and a cam groove follower defined on said blade means that rides in said cam groove; and retractor means associated with said casing means, said blade means and said fork means for retracting said cutting means of said blade means into said hollow of said casing means.

2. The device according to claim 1, further comprising accelerator means associated with said casing means for accelerating the fork means through said hollow of said casing means thereby causing said blade means to accelerate through said predetermined path.

3. The device according to claim 2, wherein said accelerator means includes at least one projection extending into said hollow from said casing means which cooperates with said fork means to create an opposing force that accelerates said blade means.

4. The device according to claim 1, wherein said blade means includes detachable blade protector means that covers said cutting portion of said blade means prior to activation of said device.

5. The device according to claim 4, wherein said blade protector means is frangibly connected to said blade means.

6. The device according to claim 1, further comprising locking means for preventing inadvertent activation of the device.

7. The device according to claim 1, wherein said retractor means includes fork spreading means defined on interior surfaces of said casing means, wherein said fork means coacts with said fork spreading means during said predetermined path to initiate said retracting of said cutting portion of said blade means, said fork spreading means operating to enable said fork means to spread thereby causing said cutting portion of said blade means to retract into said casing means.

8. The device according to claim 7, wherein said fork spreading means includes cam means which coact with an enlarged section of said blade means thereby causing said cutting portion of said blade means to retract into said casing means.

9. The device according to claim 7, wherein said fork spreading means includes a dog-leg shaped channel defined by said casing means.

10. A self-activated blood drop generator device comprising:

a casing having an internal hollow;

a blade assembly disposed within said hollow of said casing for generating an incision in a patient's skin, wherein upon the activation of said device, said blade assembly follows a predetermined path which causes a blade encased in said blade assembly to travel out of said hollow of said casing through an aperture defined in an end of said casing to incise the patient's skin and then retract back through said aperture into said hollow of said casing;

triggering means for propelling said blade assembly through said stroke, said triggering means including fork means for coupling said triggering means to said blade assembly;

accelerator means associated with said casing and said fork means for accelerating said triggering means through said hollow of said casing thereby causing said blade assembly to accelerate through said predetermined path, wherein said accelerator means includes at least one C-shaped projection extending into said hollow from said casing that cooperates with said fork means to create an opposing force that accelerates the triggering means through said hollow of said casing;

cam means associated with said casing for causing said blade to travel through an arcuate scalpel-like path as said blade means passes through said aperture in said casing; and retractor means associated with said casing, said blade assembly, and said fork means for retracting said blade into said hollow of said casing.

11. The device according to claim 10, wherein said blade is covered by detachable blade protector means prior to activation of said device.

12. The device according to claim 11, wherein said blade protector means is frangibly connected to said blade assembly.

13. The device according to claim 10, further comprising blade assembly locking means for preventing inadvertent activation of the device.

14. The device according to claim 10, wherein said cam means includes a cam groove defined in an interior surface of said casing and a cam groove follower defined on said blade assembly that rides in said cam groove.

15. The device according to claim 10, wherein said retractor means includes fork spreading means defined on interior surfaces of said casing, wherein said fork means coacts with said fork spreading means during said predetermined path to initiate said retracting of said cutting portion of said blade, said fork spreading means operating to enable said fork means to spread thereby causing said cutting portion of said blade to retract into said casing.

16. The device according to claim 15, wherein said fork spreading means includes cam means which coact with an enlarged section of said blade assembly thereby causing said cutting portion of said blade to retract into said casing.

17. The device according to claim 15, wherein said fork spreading means includes a dog-leg shaped channel defined by said casing.

18. The device according to claim 10, wherein said blade makes a scalpel-like incision in the patient's skin that is approximately 0.094 inches in depth and approximately 0.063 inches in length.

19. A self-activated blood drop generator device comprising:

casing means having an internal hollow;

blade means disposed within said hollow of said casing means for generating an incision in a patient's skin, said blade means having a cam groove follower; and a cam groove defined in an interior surface of said casing means, wherein said cam groove follower rides in said cam groove and causes said blade means to travel through an arcuate scalpel-like path when generating the incision in the patient's skin.

* * * * *